United States Patent [19]

Schumann

[11] Patent Number: Plant 5,372

[45] Date of Patent: Dec. 18, 1984

[54] GERANIUM PLANT NAMED MARS

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 548,220

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert L. Bagwill

*Attorney, Agent, or Firm*—Schwartz, Jeffery, Schwaab, Mack, Blumenthal & Koch

[57] ABSTRACT

A new and distinct cultivar of geranium named Mars characterized by the combined features of semi-double flower form and vermilion red flower color, fast rooting, excellent branching, good durability under outdoor summer conditions and good weather resistance, a lack of zonation in the leaves, and by its ability to be cultivated at temperatures below 12° C.

3 Drawing Figures

The present invention comprises a new and distinct cultivar of geranium, botanically known as *Pelargonium zonale,* and hereinafter referred to by the cultivar name Mars.

Mars is a product of planned breeding program which had the objective of creating new geranium cultivars with orange-red color, short plant height, fast rooting, good branching, durable flowers, and stable peduncles.

Mars was originated from a hybridization made in a controlled breeding program in Hillscheid, Federal Republic of Germany in 1979. The female parent was the variety Dondo Royal, an unpatented cultivar having red semi-double flowers, a large flowerhead, but less than satisfactory branching. The male parent of Mars was a cultivar derived from the self-breeding of the unpatented cultivar PAC® Alex. The male parent was selected for breeding due to its excellent branching, and red semi-double flowers carried on long peduncles.

Mars was discovered and selected as one flowering plant within the progeny of the stated cross by Ingeborg Schumann on June 27, 1980 in a controlled environment in Hillscheid, Federal Republic of Germany.

The first act of asexual reproduction of Mars was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981, and continuing into 1982 has demonstrated that the combination of characteristics as herein disclosed for Mars are firmly fixed and are retained through successive generations of asexual reproduction.

Mars has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Mars, which in combination distinguish this geranium as a new and distinct cultivar:

1. Dutch vermilion red flower color.

2. Semi-double flower form, nearly single.
3. Fast rooting.
4. An average of 7.4 branches per plant.
5. Good flower durability under outdoor summer conditions; good weather resistance.
6. Mars can be cultivated below 12° C.
7. Leaves are without zonation.

Of the many commercial cultivars known to the present inventor, the most similar in comparison to Mars are the unpatented cultivars PAC® Alex and Empress. Reference is made to attached Chart A which compares certain characteristics of Mars to those same characteristics of PAC® Alex and also to the same characteristics of the unpatented cultivars Vesuv and Rubin. In general comparison to PAC® Alex, Mars has a shorter and more stable peduncle, is more weather resistant, is different in color, and has better branching. In comparison to Empress, Mars has smaller leaves, better branching, shorter internode length and shorter plant height.

The accompanying photographic drawings show typical flower and foliage characteristics of Mars, with colors being as true as possible with illustrations of this type. Sheet 1 is a color photograph of a potted plant of Mars. Sheet 2 is a relatively enlarged color photograph of the flowers, buds and foliage, and sheet 3 is a black and white print of the underside of typical leaves of Mars.

In the following description color references are made to The Royal Horticultural Society Color Chart, with parallel or alternate values from Horticultural Color Chart (H.C.C.) being shown in certain instances. The color values were determined between 2:50–3:10 P.M. on Aug. 12, 1983 under 20,000 Klux at Hillscheid, Federal Republic of Germany.

CLASSIFICATION

Botanical: A hybrid of the genus *Pelargonium l'hert.*
Commercial: Mars.

INFLORESCENCE

Umbel:

*Average diameter.*—109 mm.
*Average depth.*—84 mm.
*Peduncle length.*—221 mm.
*Pedicel length.*—23 mm. (with ⅓ weak anthocyan).

Corolla:

*Average diameter.*—50 mm.

*Form.*—Semi-double to single; not round.

*Color (general tonality from a distance of three meters).*—R.H.S. 33A, H.C.C. 18.

*Color (abaxial).*—R.H.S. 40A, H.C.C. 717 with white eye in center of corolla.

*Color (adaxial).*—HCC 17.

Bud:

*Shape.*—Narrow elliptic

*Color (abaxial).*—A lighter red than corolla color.

Reproductive organs:

*Androecium.*—Monodelphous, 8–9 stamens; plentiful pollen.

*Gynoecium.*—Style, color red; small 4-lobed stigma, color red, deformed.

Spring flowering response period: In Hillscheid, Federal Republic of Germany in 1982, 75% of plants with at least 1 flower opened 13 weeks after planting of unrooted cuttings.

Outdoor flower production: The flower count in 1982 in Hillscheid, Federal Republic of Germany was between 44 and 46 flowers per plant for June through October observation period.

Durability: Shatter resistance good.

PLANT

Foliage:

*Form.*—Kidney shaped.

*Margin.*—Bicrenate.

*Color (abaxial).*—Medium green; no zonation.

*Tolerance to botrytis.*—Good.

General appearance and form:

*Internode length.*—31 mm.

*Branching pattern.*—Very good; an average of 7.4 branches per plant.

*Height.*—220 mm.

CHART A

| | Corolla Color | Hillscheid Spring Flowering Response | Branching Habit (number of branches) | Internode Length | Plant Height | Zonation |
|---|---|---|---|---|---|---|
| PAC ® Alex | RHS 44B blue-red eye | 55% | 5.6 | 40 mm | 270 mm | — |
| Vesuv | RHS 43B small pink eye | 50% | 3.0 | 23 mm | 220 mm | — |
| Rubin | RHS 33A inside white | 75% | 2.8 | 31 mm | 250 mm | weak |
| Mars | RHS 33A white eye | 75% | 7.4 | 31 mm | 220 mm | — |

| | Umbel Average Diameter | Average Depth | Peduncle Length | Pedicle Length | Corolla Average Diameter |
|---|---|---|---|---|---|
| Alex | 106 mm | 74 mm | 250 mm | 24 mm | 49 mm |
| Vesuv | 109 mm | 73 mm | 200 mm | 30 mm | 51 mm |
| Rubin | 108 mm | 73 mm | 213 mm | 39 mm | 54 mm |
| Mars | 109 mm | 84 mm | 221 mm | 23 mm | 50 mm |

I claim:

1. A new and distinct cultivar of geranium named Mars, as described and illustrated, and principally characterized by the combined features of semi-double flower form and vermilion red flower color, fast rooting, excellent branching, good durability under outdoor summer conditions and good weather resistance, a lack of zonation in the leaves, and by its ability to be cultivated at temperatures below 12° C.

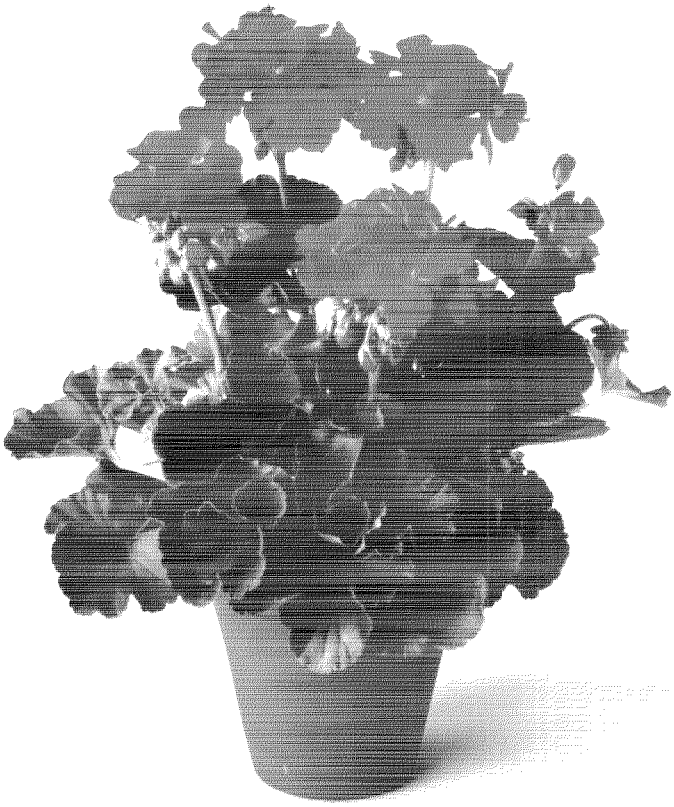

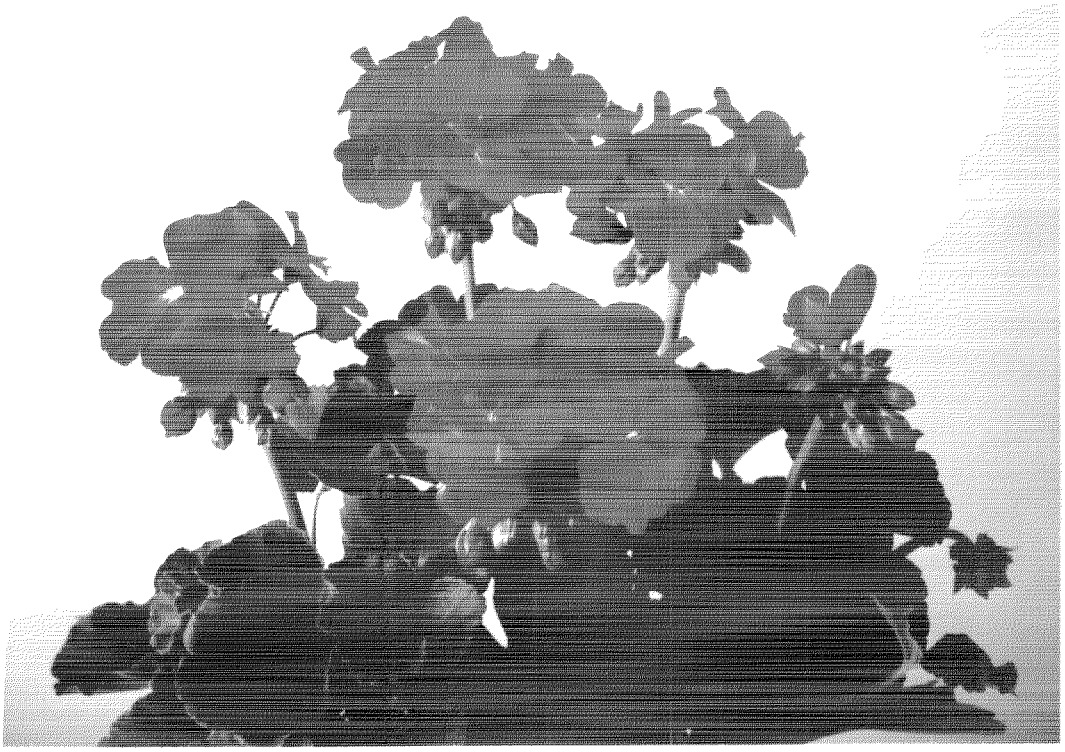

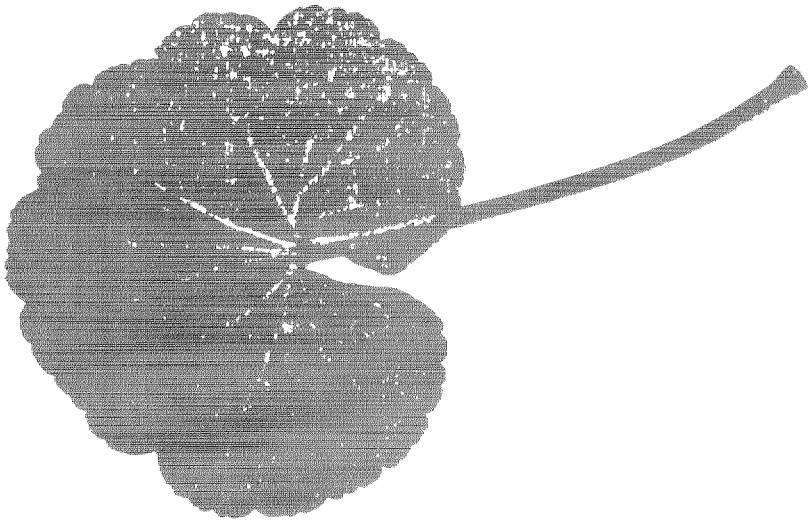
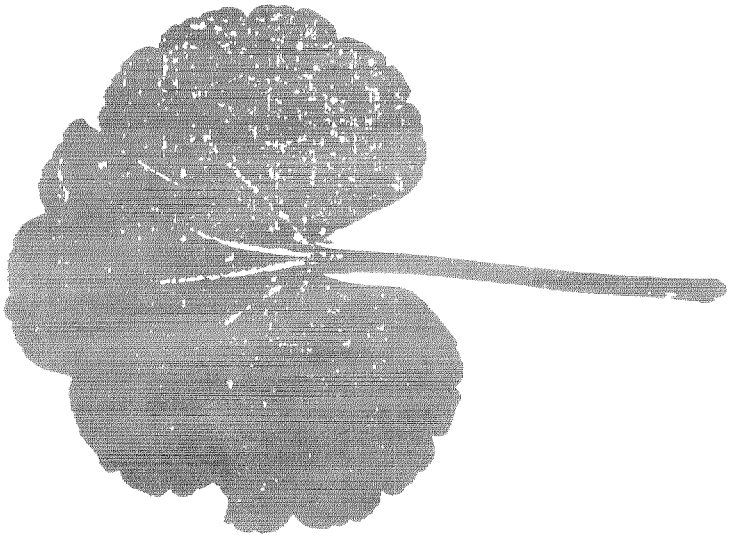

* * * * *